United States Patent [19]

Suminami et al.

[11] Patent Number: 5,783,422
[45] Date of Patent: Jul. 21, 1998

[54] DNA FRAGMENT CODING FOR SQUAMOUS CELL CARCINOMA-ASSOCIATED ANTIGEN

[75] Inventors: Yoshinori Suminami; Hiroshi Kato, both of Ube; Kiyoshi Sekiguchi; Katsumichi Takeda, both of Matsudo, all of Japan

[73] Assignee: Dainabot Co., Ltd., Japan

[21] Appl. No.: 568,147

[22] Filed: Dec. 6, 1995

Related U.S. Application Data

[62] Division of Ser. No. 99,259, Jul. 29, 1993, abandoned, which is a continuation of Ser. No. 800,952, Dec. 2, 1991, abandoned.

[30] Foreign Application Priority Data

Nov. 30, 1990 [JP] Japan ................................. 2-330155

[51] Int. Cl.$^6$ ............................ C12P 21/02; C12N 15/12; C12N 15/11
[52] U.S. Cl. ................ 435/69.3; 435/252.3; 435/252.33; 435/255.1; 435/320; 435/254.2; 536/235; 536/24.31
[58] Field of Search ............................... 435/69.3, 252.3, 435/252.33, 255.1, 320.1, 254.2; 536/23.5, 24.31

[56] References Cited

U.S. PATENT DOCUMENTS

| 4,289,690 | 9/1981 | Pestka et al. |
| 4,879,213 | 11/1989 | Fox et al. |
| 5,019,497 | 5/1991 | Olsson |

FOREIGN PATENT DOCUMENTS 62-084100  4/1987  Japan.

OTHER PUBLICATIONS

Matsuda, H. et al. (1990) *Cancer* 65:2261–2265. Immunohistochemical Evaluation of Squamous Cell Carcinoma Antigen and S–100 Protein Positive Cells in Human Malignant Esophageal Tissues.

Yagi, H. et al. (1987) *Arch. Dermatol.* 123:902–906. Significance of Squamous Cell Carcinoma (SCC)–Related Antigens in Cutaneous SCC.

Crombach, G. et al. (1989) *Cancer* 63:1337–1342. Detection of Squamous Cell carcinoma Antien in Normal Squamous Epithelia and in Squamous Cell Cacrinomas of the Uterine Cervix.

Mino, K. et al. (1988) *Cancer* 62:730–734. Availability of Tumor–Antigen 4 as a Marker of Squamous Cell Carcinoma of the Lung and Other Organs.

Bowie, J. et al. (1990) *Science* 247:1306–1310. Deciphering the Message in Protein Squences: Tolerance to Amino Acid Substitutions.

Senekjian, E. et al. (1987) *Am. J. Obstet. Gynecol.* 157:433–439. An Evaluation of Squamous Cell Carcinoma Antigen in Patients with Cervical Squamous Cell Carcinoma.

Kumar, V. et al. (1990) *Proc. Natl. Acad. Sci. USA* 87:1337–1341. Amino Acid Variations at a Single Residue in an Autoimmune Peptide Profoundly Affect is Properties: T–Cell Activation, Major Histocompatibility Complex Binding, and Ability to Block Experimental Allergic Encephalomyelitis.

Fernstein, P. et al. (1986) *Cancer Research* 46:2970–2977. Antigens Associated with Human Squamous Cell Lung Carcinoma Defined by Murine Monoclonal Antibodies.

Sambrook et al. (1989) *Molecular Cloning: A Laboratory Manual* 2:12.2–12.44 Cold Spring Harbor Laboratory, Cold Spring Harbor, NY.

Obata, K. et al. (1988) *Clinical Chemistry* 34(6):1300 – Abstract No. 719.

Takebe et al. Biochem. Biophys. Resc. Comm. 143(3):837–844, Mar. 1987.

Nikolimkou et al. Gene 30: 261–65, 1984.

*Primary Examiner*—Anthony C. Caputa
*Attorney, Agent, or Firm*—Scully, Scott, Murphy & Presser

[57] ABSTRACT

A DNA fragment coding for squamous cell carcinoma-associated antigen is first isolated and prepared by DNA recombination techniques. The fragments thus obtained are useful as diagnostic reagents for the squamous cell carcinoma and as immunogens.

6 Claims, 8 Drawing Sheets

Fragment 10:

Val Leu Glu Ile Pro Tyr Lys

Fragment 13:

Tyr Leu Phe Leu [Phe or Gln] Tyr Glu Arg Phe Ser Val Pro

Fragment 19:

Gly Met Val X <u>Ile Phe Asn Gly Asp Ala</u> Asp Leu (Ser) Gly Met Thr Gly (Ser) Arg Gly Leu Val Leu

Fragment 21-1:

X Leu Ser Met Ile Val Leu Leu <u>Pro Asn Gln Ile Asp Gly</u> Leu Gln Lys

Fragment 21-2:

X Met Phe X Leu Phe Gln Gln Phe Arg Lys

Fragment 26:

(Phe) Met Phe (Asp) Leu Phe

FIG.1

Primer 1:

5'-GCGTCTCCGTTGAATAT-3'
       A G      A G
       C        A
       A

Primer 2:

5'-ATATTCAACGGAGACGC-3'
       C T      C T
       T        G
                T

Primer 3:

5'-CCAAACCAAATAGACGG-3'
       G T G    C T
       C        T
       T

Primer 4:

5'-CCGTCTATTTGGTTTGG-3'
       A G C A  C
         A      G
                A

Primer 5:

5'-TTTCTAGAACAGATTCCACACTGGTCTGG-3'
       ‾‾‾‾‾‾
        Xba I

Primer 6:

5'-TTTCTAGAGATCTTCAGCTCATATGCATC-3'
       ‾‾‾‾‾‾
        Xba I

Primer 7:

5'-GGGAGCTCGCTGGGTAGTCCCCACCTTT-3'
       ‾‾‾‾‾‾
        Sac I

Primer 8:

5'-GGGAGCTCCTTATGAGTATTTCTTCCAGGGTA-3'
       ‾‾‾‾‾‾
        Sac I

FIG. 2

5'-CGAGCTGCTC TATAGACTGC TGGGTAGTCC CCACCTTTTG AGCAAGTTCA GCCTGGTTAA
3'-GCTCGACGAG ATATCTGACG ACCCATCAGG GGTGGAAAAC TCGTTCAAGT CGGACCAATT

```
         GGGAGCTCGC TGGGTAGTCC CCACCTTT
      5' GGGAGCTC    Primer 7       →
            SacI
```

```
                                                    Primer 8                    5'
                                         ←
                              ATGGG ACCTTCTTTA TGAGTATTCC TCGAGCG
    EcoRI                                                       SacI
GTCCAAGCTG AATTCTTTTG CTTTTTACCC TGGAAGAAAT ACTCATAAGC CACCTCTGTT-3'
CAGGTTCGAC TTAAGAAAAC GAAAAATGGG ACCTTCTTTA TGAGTATTCG GTGGAGACAA-5'
```

FIG. 3

```
5'-C TCT CTG CCC ACC TCT GCT TCC TCT AGG AAC

ATG TTC GAC CTG TTC CAA CAG TTC AGA AAA TCA
Met Phe Asp Leu Phe Gln Gln Phe Arg Lys Ser

GGA GCC AAA GAC AAC ACT GCA CAA CAG ATT AAG
Gly Ala Lys Asp Asn Thr Ala Gln Gln Ile Lys

GAT AGG TCA GGA AAT GTT CAT CAC CAG TTT CAA
Asp Arg Ser Gly Asn Val His His Gln Phe Gln

TTC GGA GAA AAA ACG TAT CTA TTT TTA CAG GAA
Phe Gly Glu Lys Thr Tyr Leu Phe Leu Gln Glu

CCA GAA GAA AGT CGA AAG AAG ATT AAC TCC TGG
Pro Glu Glu Ser Arg Lys Lys Ile Asn Ser Trp

ACC ACA TTG GTT CTT GTG AAC GCA ATC TAT TTC
Thr Thr Leu Val Leu Val Asn Ala Ile Tyr Phe

AAG AAT ACA TAC AAG TCC ATA CAG ATG ATG AGG
Lys Asn Thr Tyr Lys Ser Ile Gln Met Met Arg

TAC AAA GGC AAA GAT CTA AGC ATG ATT GTG TTG
Tyr Lys Gly Lys Asp Leu Ser Met Ile Val Leu

GAA TGG ACA AGT TTG CAG AAT ATG AGA GAG ACA
Glu Trp Thr Ser Leu Gln Asn Met Arg Glu Thr

AGA ACC ATG GGA ATG GTG GAT ATC TTC AAT GGG
Arg Thr Met Gly Met Val Asp Ile Phe Asn Gly

GCC TTT GTG GAG GTT ACA GAG GAG GGA GCA GAA
Ala Phe Val Glu Val Thr Glu Glu Gly Ala Glu

CAT TGT AAT CAC CCT TTC CTA TTC TTC ATA AGG
His Cys Asn His Pro Phe Leu Phe Phe Ile Arg

TGT CAC TCC ATT TGG AAA ATG TTC ACC TGC AGA

ATC TTG ATG ATG ATC GTC ATC ATC AAG AAT TTA

CTT CCA GAA AAA TTC TCC TTG AGG AAA AAT GTC

CTG TTT TAA ATG AAC CAA ACC AAA TCA TAC TTT

CTT ATG TTT CTA AAT TTT GTG ATT CTA TAA AAC
```

FIG.4A

```
ACA GGA GTT CCA GAT CAC ATC GAG TTC ACC ATG
                                            Met

AAA GAG AAC AAC ATC TTC TAT TCC CCT ATC AGC
Lys Glu Asn Asn Ile Phe Tyr Ser Pro Ile Ser

AAG GTT CTT CAC TTT GAT CAA GTC ACA GAG AAC
Lys Val Leu His Phe Asp Gln Val Thr Glu Asn

AAG CTT CTG ACT GAA TTC AAC AAA TCC ACT GAT
Lys Leu Leu Thr Glu Phe Asn Lys Ser Thr Asp

TAT TTA GAT GCC ATC AAG AAA TTT TAC CAG ACC
Tyr Leu Asp Ala Ile Lys Lys Phe Tyr Gln Thr

GTG GAA AGT CAA ACG AAT GAA AAA ATT AAA AAC
Val Glu Ser Gln Thr Asn Glu Lys Ile Lys Asn

AAA GGG CAG TGG GAG AAG AAA TTT AAT AAA GAA
Lys Gly Gln Trp Glu Lys Lys Phe Asn Lys Glu

CAA TAC ACA TCT TTT CAT TTT GCC TCG CTG GAG
Gln Tyr Thr Ser Phe His Phe Ala Ser Leu Glu

CTG CCA AAT GAA ATC GAT GGT CTC CAG AAG CTT
Leu Pro Asn Glu Ile Asp Gly Leu Gln Lys Leu

CGT GTC GAT TTA CAC TTA CCT CGG TTC AAA GTG
Arg Val Asp Leu His Leu Pro Arg Phe Lys Val

GAT GCA GAC CTC TCA GGC ATG ACC GGG AGC CGC
Asp Ala Asp Leu Ser Gly Met Thr Gly Ser Arg

GCT GCA GCT GCC ACC GCT GTA GTA GGA TTC GGA
Ala Ala Ala Ala Thr Ala Val Val Gly Phe Gly

CAA AAT AAG ACC AAC AGC ATC CTC TTC TAT GGC
Gln Asn Lys Thr Asn Ser Ile Leu Phe Tyr Gly

TGT TCT GGT AAA CTG ATT GCT GGC AAC AAC AGA

ATG ATT AAA ATA GCA TGC CTT TCT CTC TTT CTC

CAA AAT AAG ATG AAT CAC TTA ATA CCG TAT CTT

TTC TTT GAA TTT AGC AAC CTA GAA ACA CAC ATT

ACA TCA TCA ATA AAA TAG TGA CAT AAA ATC AAA
```

FIG.4B

```
AAT TCA CTC AGT GAA GCC AAC ACC AAG TTC      94
Asn Ser Leu Ser Glu Ala Asn Thr Lys Phe      11

ATC ACA TCA GCA TTA GGG ATG GTC CTC TTA     190
Ile Thr Ser Ala Leu Gly Met Val Leu Leu      43

ACC ACA GGA AAA GCT GCA ACA TAT CAT GTT     286
Thr Thr Gly Lys Ala Ala Thr Tyr His Val      '75

GCA TAT GAG CTG AAG ATC GCC AAC AAG CTC     382
Ala Tyr Glu Leu Lys Ile Ala Asn Lys Leu     107

AGT GTG GAA TCT GTT GAT TTT GCA AAT GCT     478
Ser Val Glu Ser Val Asp Phe Ala Asn Ala     139

CTA ATT CCT GAA GGT AAT ATT GGC AGC AAT     574
Leu Ile Pro Glu Gly Asn Ile Gly Ser Asn     171

GAT ACT AAA GAG GAA AAA TTT TGG CCA AAC     670
Asp Thr Lys Glu Glu Lys Phe Trp Pro Asn     203

GAT GTA CAG GCC AAG GTC CTG GAA ATA CCA     766
Asp Val Gln Ala Lys Val Leu Glu Ile Pro     235

GAA GAG AAA CTC ACT GCT GAG AAA TTG ATG     862
Glu Glu Lys Leu Thr Ala Glu Lys Leu Met     267

GAA GAG AGC TAT GAC CTC AAG GAC ACG TTG     958
Glu Glu Ser Tyr Asp Leu Lys Asp Thr Leu     299

GGT CTC GTC CTA TCT GGA GTC CTA CAC AAG    1054
Gly Leu Val Leu Ser Gly Val Leu His Lys     331

TCA TCA CCT GCT TCA ACT AAT GAA GAG TTC    1150
Ser Ser Pro Ala Ser Thr Asn Glu Glu Phe     363

AGA TTC TCA TCC CCG TAG ATG CAA TTA GTC    1246
Arg Phe Ser Ser Pro ***                     390

TTC TCT TGG CTC ATA TTT CTT TTC TTT CTC    1342

TTA ATA AGC CCA CAT ATA AAT GTA CTT TTT    1438

CTA AAT TTG AAA TAT AAT TCT GTT TGT GAC    1534

TAT TTG AAT TTA GGT GAT ACC TAA ATC CTT    1630

AAA AAA AAA AAA AAA -3'                    1711
```

DNA FRAGMENT CODING FOR SQUAMOUS CELL CARCINOMA-ASSOCIATED ANTIGEN

This is divisional of application Ser. No. 08/099,259, filed Jul. 29, 1993, now abandoned, which is a FWC of Ser. No. 07/800,952, filed Dec. 2, 1991, now abandoned.

FIELD OF THE INVENTION

The present invention relates to a DNA fragment coding for squamous cell carcinoma-associated antigen (hereinafter referred to as SCC antigen).

More specifically, the invention relates to a DNA fragment which comprises a gene (complementary DNA or cDNA) for the SCC antigen extracted and refined from the squamous cell carcinoma tissue of uterine cervix.

BACKGROUND OF THE INVENTION

The SCC antigen is a protein having a molecular weight of about 45,000 obtained by the SDS-polyacrylamide gel electrophoresis, and is squamous cell carcinoma-associated antigen which is extracted and refined from the squamous cell carcinoma tissue of uterine cervix, lung cancer, or esophageal carcinoma, or the transitional lesion thereof. The SCC antigen is measured by the immunological measuring method in order to diagnose squamous cell carcinoma, to effect prognostic presumption, and to control the condition of the disease.

When the SCC antigen is to be used as a diagnostic reagent, the SCC antigen must be used in large amounts. However, it is not necessarily a desirable method to refine large amounts of antigen from the human cancerous cells.

Furthermore, it is essential to obtain a gene fragment which codes for the SCC antigen in order to detect the SCC antigen related genes by the hybridization of nucleic acid or to produce the SCC antigen by the recombinant DNA technology.

SUMMARY OF THE INVENTION

The present invention is to provide a gene which codes for the SCC antigen.

The present invention makes it possible to detect an SCC antigen related gene by the hybridization of nucleic acid. Moreover, the SCC antigen obtained by utilizing the present invention can be used as a diagnostic reagent for the squamous cell carcinoma or as an immunogen.

The present inventors have succeeded for the first time in isolating and obtaining a gene which codes for the SCC antigen. The gene which codes the SCC antigen of the present invention can be obtained by, for example, a method described hereinbelow.

First, the cervical carcinoma cell line SKG-IIIa [Cancer Res., 43, pp. 1748–1760, 1983] which is an SCC antigen-producing culture cell is denatured with guanidine thiocyanate, and is homogenized. Then, the total RNA is isolated as a pellet after sedimentation through a cesium chloride solution by density gradient centrifugation in compliance with Chirgwin et al. method [Biochemistry, 18, pp. 5294–5299, 1979]. After isolated, the total RNA is extracted with phenol and is refined by the precipitation in ethanol.

BRIEF DESCRIPTION OF THE DRAWINGS

FIG. 1 shows amino acid sequences (SEQ ID NOS:12–17) of SCC that has been partly determined. The underlined portions represent sequences that correspond to the primers 1, 2 (fragment 19) (SEQ ID NOS:3,4 and 14, respectively) and, primers 3, 4 (fragment 21-1) (SEQ ID NOS:5, 6 and 15, respectively), and X denotes amino acid which has not been confirmed yet, and parentheses represent amino acids that are estimated.

FIG. 2 shows oligodeoxynucleotide primers for PCR. The primers 1 and 4 (SEQ ID NO:3 and SEQ ID NO:6) are mixed primers in agreement with the sequences of the sense chain side estimated from the amino acid sequences underlined in FIG. 1, and the primers 2 and 3 (SEQ ID NO:4 and SEQ ID NO:5) are mixed primers in agreement with the sequences of the anti-sense chain side. The primers 5 and 6 (SEQ ID NO:7 and SEQ ID NO:8) are unique primers in agreement with the base sequence of the 5' side of λSCC1 and the primers 7 and 8 (SEQ ID NO:9 and 10) are unique primers in agreement with the base sequences of the upstream side and downstream side of EcoRI restriction site of the λgt 10 vector. The XbaI site was added to the primers 5 and 6 on the 5' side and the SacI site was added to the primers 7 and 8 on the 5' terminal side.

FIG. 3 shows the EcoRI restriction site of the λgt 10 vector (SEQ ID NO:11) and the sites where primers 7 and 8 are hybridized.

FIG. 4 shows amino acid sequences that are estimated to be base sequences of SCC antigen cDNA. The nucleotide sequence of the cDNA for an SCC antigen of the present invention is provided by SEQ ID NO:1. The corresponding amino acid sequence is provided by SEQ ID NO:2. The pcSCC2 is from nucleotide No. 1 to No. 370 of the upper sequence, and λSCC1 is from 64 to 1711. Amino acid sequences are shown under the base sequences. Arrows indicate positions of the primers 6, 5, 3 and 1 in this order from the 5' terminal side. Portions indicated by boxes represent those portions (fragments 21-2=26, 10, 21-1, 19 (SEQ ID NOS:16, 17, 12, 15 and 14, respectively) in this order from the N terminal side) that are in agreement with the amino acid sequences of SCC antigen that has been partly determined. A dotted line represents a site which is in agreement with an sequence (Asn-X-Ser/Thr) to which aspartic-bonded sugar chains can be bonded. A double underline represents a poly(A) signal.

DETAIL DESCRIPTION OF THE INVENTION

Figure 5:
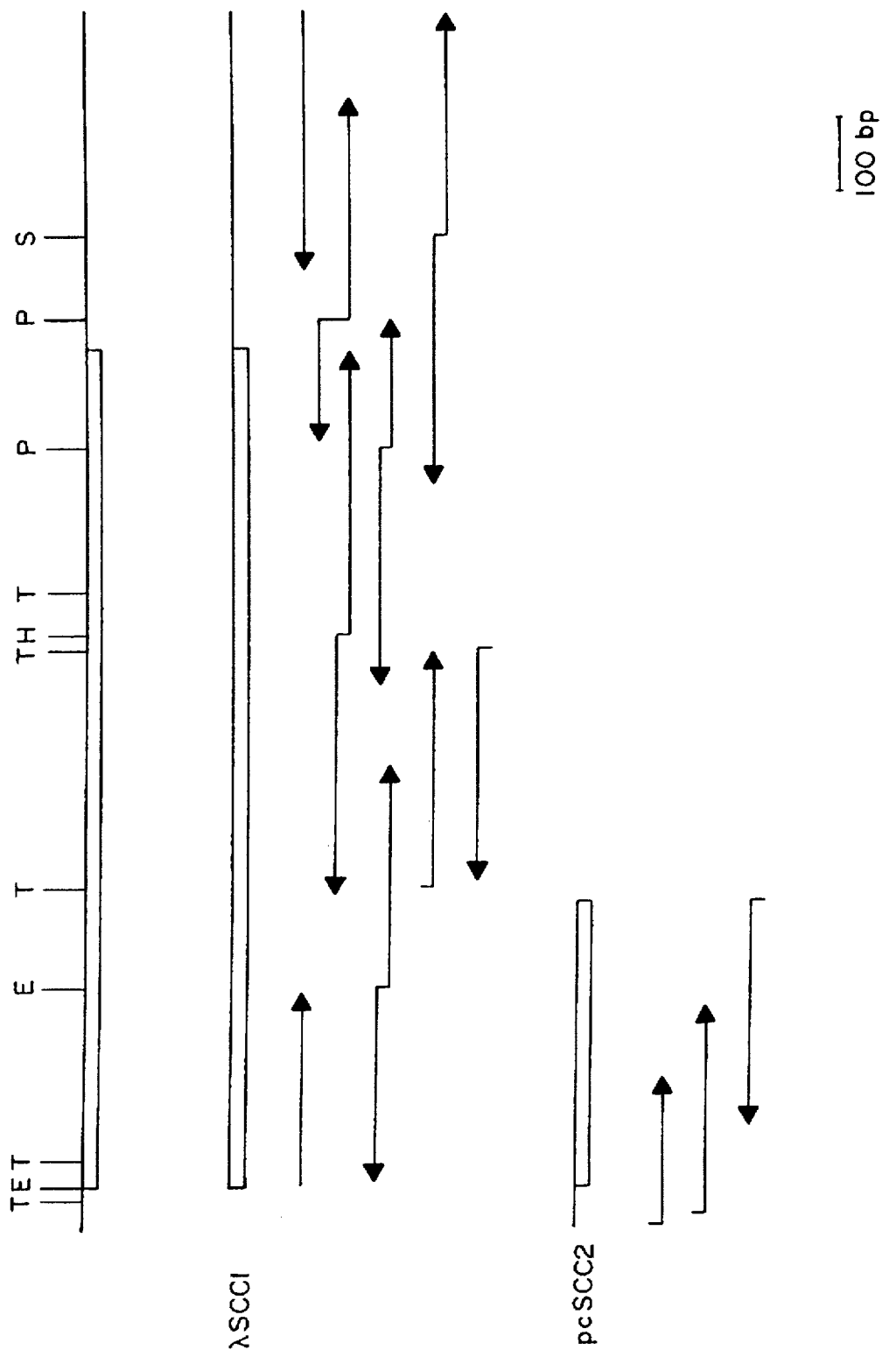
FIG. 5 shows a restriction map of λSCC1 and pcSCC2, wherein the left side is 5' terminus, the right side is 3' terminus, boxes represent translational regions, horizontal lines represent non-translational regions, vertical lines represent sites of restriction enzymes used for cleaving DNA, arrows represent regions and directions of the sequences, symbol T denotes TaqI, E denotes EcoRI, H denotes HindIII, P denotes PstI, and S denotes SphI.

The present invention relates to a DNA fragment coding for squamous cell carcinoma-associated antigen (hereinafter referred to as SCC antigen).

More specifically, the invention relates to a DNA fragment which comprises cDNA for the SCC antigen extracted and refined from the squamous cell carcinoma tissue of uterine cervix.

According to the present invention, the source for mRNA is not limited to the squamous cell carcinoma but includes, depending upon the cases, those which are widely known as SCC antigen-producing cells or tissues. Examples of such cells or tissues include squamous cell carcinoma cells or cell lines derived therefrom. Moreover, once the DNA sequence of the present invention is obtained, there is no particular limitation on the starting cells.

According to the present invention, furthermore, the DNA fragment and the cDNA library can be suitably obtained from the gene source cells by using a commercially available mRNA isolation kit, cDNA synthesizing kit, or cDNA cloning system kit. Commercially available examples include RNA extraction kit (commercially sold by Amersham), Oligotex-dT30 (commercially sold by Nippon Rosche Co., Japan), cDNA synthetic System Plus (commercially sold by Amersham), cDNA Cloning System λgt 10 (commercially sold by Amersham), and Gene Amp™ DNA Amplification Reagent Kit (commercially sold by Takara Shuzo Co., Japan) to which, however, the present invention is in no way limited.

Most of the mRNA in the cell have a poly(A) sequence at the 3'-terminal. Poly(A)-lacking RNAs such as rRNA and the like are removed by an oligo(dT)-cellulose column or an oligo(dT)-latex complex, and poly(A)-containing RNA (poly(A$^+$) RNA) is isolated and is used as a starting material mRNA. A complementary DNA (cDNA) is prepared from the starting material mRNA, a DNA fragment is obtained from the cDNA by the PCR (polymerase chain reaction), and a cDNA library is prepared by the cloning.

A desired clone which includes a DNA fragment coding for the SCC antigen is screened from the thus prepared cDNA library. The screening of cDNA consists of selecting two appropriate portions from the partially determined amino acid sequence of SCC antigen, chemically synthesizing the entire codon sequence that are presumed relative thereto to form a primer, and subjecting the thus obtained primer and the above-mentioned cDNA to the PCR, in order to obtain a DNA fragment. The obtained DNA fragment is treated with T4 polynucleotide kinase, ligated with M13 phage vector, transfected into *Escherichia coli*, for example, *Escherichia coli* JM109 strain, as a host, and the base sequence is determined in compliance with Sanger et al. method [Pro. Natl. Acad. Sci., 74, pp. 5463–5467, 1977] to select a DNA fragment which codes for the amino acid sequence in agreement with the amino acid sequence of SCC antigen which has been partly determined in advance. The above-mentioned cDNA library is further screened using the DNA fragment as a probe, thereby to obtain a clone.

The DNA sequence according to the present invention can be identified, cloned, or can further be determined in compliance with the methods disclosed in Maniatis et al., Molecular Cloning, A Laboratory Manual, Cold Spring Harbor Laboratory, 1982, or in compliance with the methods disclosed in the references quoted in the above literatures.

When the base sequence of the obtained clone was first determined in the present invention, it was found that there was contained no translational initiation region. Then, the present inventors have designed and prepared unique primers, i.e. primers that correspond to the base sequence on the 5' terminal side of the clone and ones that correspond to the base sequence on the upstream side and downstream side of the EcoRI restriction site of λgt 10. These primers are subjected to the PCR using as a template the DNA fragment prepared from the above cDNA library to afford DNA fragment clones.

The base sequence of the obtained clone is subcloned into M13 mp18 or M13 mp19, and is determined by Sanger et al. method.

According to the present invention, the DNA sequence once obtained as described above can be used for a variety of applications without modifying the sequence or with suitably modifying the sequence. Examples of the modification include cleavage, substitution, deletion, addition and ligation. A preferred example of the modification method may be a site-directed mutagenesis such as the one disclosed in Lather, R. F. and Lecoq, L. P., Genetic Engineering, Academic Press, pp. 31–50, 1983. The base sequence can be cleaved by using a variety of restriction enzymes that are available in the market.

The DNA sequence obtained according to the present invention can be used entirely or partly as a DNA probe. When used as a DNA probe, it can be labelled with a suitable labelling agent such as a radioactive isotope, enzyme, fluorescent agent, coloring agent, or the like. Here, the labelling agent may be attached via a suitable spacer. Representative examples of the DNA sequence used as the DNA probe include those used for screening the DNA libraries in the embodiment herein.

The DNA sequence according to the present invention is inserted or ligated into a suitable expression vector and is introduced into a suitable host cell so as to be expressed. Examples of the expression vectors include those vectors for *E. coli*, yeast and mammal cells.

The DNA of the present invention can be expressed in *E. coli* to give a protein that exhibits positive reactivity by SCC antigen detecting kit and positive band on the Western blotting using monoclonal antibodies specific to SCC antigen. The DNA fragment carrying the base sequence coding for squamous cell carcinoma-associated antigen proteins of the present invention has been harbored into *E. coli* which is deposited in the Fermentation Research Institute Agency of Industrial Science and Technology, MITI, Japan, as Microorganism Deposit Accession No. 11871 (FERMP-11871).

The protein product thus obtained can be used as an antigenic reagent for measurement or as an immunogen.

The amino acid sequence encoded by the DNA sequence of the present invention has four sites for binding a sugar group, i.e., Asn-X-Ser/Thr where aspartic-coupled sugar chains can be bonded. Therefore, there is a possibility of obtaining many proteins with different molecular weights if the DNA sequence is expressed using various hosts. When the amino acid sequence encoded by the DNA sequence are retrieved for their homology using the data base of a computer (DNASIS, Hitachi, Japan), it has been found that they are entirely homologous to the serine protease inhibitor family (Serpins Family). It was therefore confirmed that they can be used as therapeutic drugs.

It will therefore be obvious that the DNA sequence according to the invention (SEQ ID NO:1) and the applications which utilize information related thereto are all encompassed within the spirit and scope of the present invention.

The foregoing is merely illustrative of the invention and is not intended to limit the invention to the disclosure.

EXAMPLES

By the following examples, the present invention will be explained more concretely, but they should not be interpreted as limiting the invention in any manner.

Example 1

Preparation of cDNA and a library thereof from SCC antigen-producing cell line SKG-IIIa.

(1) Extraction of the total RNA.

An RNA was extracted from the cultured SCC antigen-producing cell line SKG-IIIa using an RNA extraction kit (Amersham). The SCC antigen-producing cell line SKG-IIIa cells (1.7×10⁸ cells) were homogenized by using a solution 1 of the kit (a Tris-hydrochloric acid buffer solution containing guanidine thiocyanate and EDTA, pH 7.4) to which 2-mercaptoethanol was added. After treated with ultrasonic vibration for 40 seconds, the cooled ethanol (−20° C.) was added thereto in an amount of 0.3 times thereof, and the mixture was centrifuged to 10,000×g at 0° C. for 5 minutes. After the centrifugation, the protein layer and the supernatant fluid were removed. The RNA pellet was resuspended in 10 ml of the solution 1 containing 2-mercaptoethanol, and was retreated with ultrasonic vibration for 40 seconds. After the treatment, about 30 ml of a solution 2 (aqueous solution of lithium chloride) was added thereto, and the mixture was allowed to stand overnight at 4° C., and was then subjected to the centrifugation of 10,000×g at 4° C. for 90 minutes. The protein layer and the supernatant fluid on the surface were removed. Thirty-five ml of solution 3 (aqueous solution of lithium chloride-urea) was added to the RNA pellet, and the mixture was vortex-treated for 30 seconds and was immersed in a hot bath maintained at 40° C. for about 45 minutes. The suspension was recentrifuged to 10,000×g at 4° C. for 60 minutes, and the protein layer and the supernatant fluid were removed. To the RNA pellet was added 5 ml of a solution 4 (RNA buffer solution) and the mixture was allowed to stand at −20° C. for about two hours.

The mixture was vortex-treated for 30 seconds and was immersed in the hot bath maintained at 40° C. for about 45 minutes, so that the precipitate was suspended again. A phenol solution saturated with a 0.1M Tris-hydrochloric acid buffer solution (pH 7.4) was added in an amount of 5 ml thereto, and the mixture was vortex-treated for 10 seconds. Furthermore, after mildly blended for 20 minutes, the mixture was centrifuged to 8,500×g at room temperature for 15 minutes. The liquid of the upper layer was collected and to which was added 5 ml of phenol solution saturated with 0.1M Tris-hydrochloric acid buffer solution (pH 7.4). The mixture was vortex-treated for 10 seconds, mildly blended for another 20 minutes, and was centrifuged to 8,500×g at room temperature for 15 minutes. The fluid of the upper layer was collected and to which was added 5 ml of a chloroform solution, and the mixture was vortex-treated for 5 seconds. The mixture was centrifuged to 8,500×g at room temperature for 10 minutes, and the fluid of the upper layer was collected. To the fluid was added 2M sodium acetate (pH 5.0) in an amount of 0.1 as a volume ratio and ethanol in an amount of two folds as much, and the precipitation took place at −20° C. overnight.

The RNA precipitate was centrifuged to 8,500×g at 4° C. for 30 minutes, the supernatant fluid was discarded away, and to the remaining solution was added 1 ml of a cooled 70% (v/v) ethanol solution (−20° C.), and the mixture was centrifuged to 8,500×g at 4° C. for 15 minutes. The supernatant fluid was removed, the RNA pellet was dried with the air and was dissolved in 1 ml of sterilized water. The total RNA in an amount of 366 µg were obtained (2) Isolation of poly(A)⁺ RNA.

A poly(A)⁺ RNA was refined two times from the thus obtained total RNA by using Oilgotex-dT30(Nippon Rosche Co., Japan).

That is, 296, µg of the total RNA was precipitated in ethanol, dissolved in 800 µl of TE buffer (10 mM Tris-hydrochloric acid buffer solution (pH 7.5) containing 1 mM EDTA) and 0.1% SDS (sodium dodecyl sulfate), heat-treated at 65° C. for 5 minutes, and was quenched in ice. One hundred µl of 5M sodium chloride was added thereto followed by being mixed with 200 µg 1 (4 mg) of Oligotex-dT30. The mixture solution was incubated at 37° C. for 5 minutes, centrifuged to 15,000 rpm at room temperature for 10 minutes, and the supernatant fluid was removed. To the obtained pellets were added 100 µl of a 5M sodium chloride solution and 1 ml of TE buffer (pH 7.5) and 0.1% SDS, followed by pipetting, in order to obtain a homogeneous suspension. After incubated at 37° C. for 5 minutes, the suspension was centrifuged to 15,000 rpm at room temperature for 10 minutes, and the supernatant fluid was removed. To the obtained pellets was added 800 µl of TE buffer (pH 7.5) and 0.1% SDS, and the mixture was heat-treated at 65° C. for 5 minutes and was centrifuged to 15,000 rpm for 10 minutes to obtain the supernatant fluid. The supernatant fluid was heated at 65° C. for 5 minutes and was quenched in ice. One hundred µl of 5M sodium chloride was added thereto followed by being mixed with 200 µl (4 mg) of Oligotex-dT30. The mixture solution was incubated at 37° C. for 5 minutes and was centrifuged to 15,000 rpm at room temperature for 10 minutes in order to remove the supernatant fluid. To the obtained pellets were added 100 µl of 5M sodium chloride and 1 ml of TE buffer (pH 7.5) and 0.1% SDS, followed by pipetting to obtain a homogeneous suspension. After incubated at 37° C. for 5 minutes, the suspension was centrifuged to 15,000 rpm at room temperature for 10 minutes to remove the supernatant fluid. To the obtained pellets was added 800 µl of TE buffer (pH 7.5) and 0.1% SDS, and the mixture was heat-treated at 65° C. for 5 minutes and was centrifuged to 15,000 rpm for 10 minutes to obtain the supernatant fluid. The supernatant fluid was extracted with an equal amount of a mixed solution of phenol and chloroform (1:1, v/v), and was precipitated in ethanol. The obtained pellets were dissolved in 100 µl of 3M sodium acetate (pH 5.6) followed by the addition of 200 µl of ethanol, and was allowed to stand at −80° C. for 30 minutes. The mixture was centrifuged to 15,000 rpm at 4° C. for 10 minutes to obtain pellets of poly(A)⁺ RNA. The pellets were washed with 70% ethanol, dried, and were dissolved in 10 µl of sterilized water.

There was obtained 3.6 µg of a poly(A)⁺ RNA.

(3) Synthesis of cDNA.

A cDNA was synthesized from the poly(A)⁺ RNA by using the oligo(dT) primer and the cDNA Synthesis System Plus (Amersham).

To 1 µg of poly(A)⁺ mRNA in an ice bath were added 4 µl of a buffer solution for the 5×first strand synthesis reaction, 1 µl of a sodium pyrophosphate solution, 1 µl of ribonuclease inhibitor of human placenta, 2 µl of a mixed solution of deoxynucleoside and triphosphate, 1 µl of oligo (dT) primer and sterilized water such that the total amount was 19 µl. It was mildly mixed and was centrifuged for several seconds using Eppendolf's rotor. A reverse transcriptase (20 units/µl) was added in an amount of 1 µl thereto, and it was mildly mixed and was incubated at 42° C. for 40 minutes. The reaction tube was returned to the ice bath, and there were added 37.5 µl of a buffer solution for the second strand synthesis reaction, 0.8 unit of E. coli ribonuclease H, 23 units of E. coli DNA polymerase I and sterilized water so that the amount was 99.5 µl. It was mildly mixed, and was reacted at 12° C. for 60 minutes and then at 22° C. for another 60 minutes. The mixture was then incubated at 70° C. for 10 minutes and was centrifuged for several seconds using Eppendolf's rotor. The mixture was returned to the ice bath and 2.0 units of T4 DNA polymerase was added thereto. It was mildly mixed and was then reacted at 37° C. for 10 minutes.

Four µl of 0.25M EDTA (pH 8.0) was added to stop the reaction. Then, 104 µl of phenol/chloroform (1:1, v/v) was added thereto, and it was vigorously mixed using a vortex mixer to obtain an emulsion thereof. The emulsion was centrifuged for one minute Eppendolf's rotor, and was separated into two layers. The aqueous layer (upper layer) was collected while giving attention in order not to collect the intermediate layer, followed again by the addition of 104 µl of a phenol/chloroform solution. It was vigorously mixed using the vortex mixer to obtain an emulsion thereof which was then centrifuged for one minute using Eppendolf's rotor and was separated into two layers. The aqueous layer (upper layer) was collected, and 104 µl of chloroform was added thereto, and it was mixed well. The mixture was centrifuged for several seconds using Eppendolf's rotor, and the aqueous layer (upper layer) was collected. One hundred four µl of 4M ammonium acetate solution was added, followed by the addition of 416 µl of ethanol cooled at −20° C., and the mixture was allowed to stand over the dry ice for 15 minutes.

While mildly mixing, the temperature was returned to room temperature and the mixture was centrifuged for 10 minutes using Eppendolf's rotor. The supernatant fluid was removed while giving attention so as not to whirl up the cDNA pellets. Then, to wash the mixture, 50 µl of 2M ammonium acetate and 100 µl of ethanol (−20° C.) were added thereto, and it was mildly mixed at room temperature and after the centrifugation, the supernatant fluid was removed by aspiration. Two hundred µl of ethanol (−20° C.) was added so as not to disturb the pellets, and it was mildly mixed at room temperature, centrifuged, and removed the supernatant fluid by aspiration. The cDNA pellet was dried and was dissolved in 10 µl of TE buffer (pH 7.5).

Thus, 1.2, µg of cDNA was prepared from 1 µg of the poly(A)⁺ RNnA.

(4) Synthesis of cDNA library.

The cDNA library was synthesized by using the cDNA cloning system λgt 10 (Amersham).

That is, to 720 ng of cDNA were added 2 µl of an L/K buffer solution, 2.5 µl of an EcoRI adaptor and the sterilized water, so that the total amount was 18 µl. It was mildly mixed and was centrifuged for several seconds using Eppendolf's rotor. Two µl of T4 DNA ligase (5 units) was added thereto, and it was mildly mixed and was reacted at 15° C. for 20 hours. Two µl of 0.25M EDTA was added to stop the reaction, and the mixture was centrifuged for several seconds using Eppendolf's rotor. The cDNA to which the EcoRI adaptor has been bonded was passed through a column attached to the kit to effect the size fractionation to obtain a selection pool, and the unreacted adaptor was removed. The obtained selection pool (900 µl), 100 µl of the L/K buffer solution, and 10 µl (80 units) of T4 polynucleotide kinase were added together, and the mixture was incubated at 37° C. for 30 minutes. After the phosphorylation, extraction was effected using an equivalent amount of phenol/chloroform (1:1, v/v) and chloroform/isoamyl alcohol (24:1) each two times. The extractions were effected under a slightly vortexed condition, and the mixture was centrifuged for one minute using Eppendolf's rotor to remove the organic solvent of the lower layer while leaving the upper water layer. To the water layer was added 2.2 parts in volume of butanol, and the mixture was vigorously shaken so as to be separated into two layer, and the upper butanol layer was removed. Extraction was effected again with butanol to concentrate the cDNA solution. The upper butanol layer was removed, and 1/10 parts in volume of 3M sodium acetate and twice as much amount of ethanol were added thereto. After mixed well, the mixture was left to stand overnight at −20 °C., and was then centrifuged for 30 minutes using Eppendolf's rotor. Thereafter, the supernatant fluid was removed. To the residue was added 0.5 ml of 70% ethanol cooled with ice. After slightly vortexed, the mixture was centrifuged for 5 minutes using Eppendolf's rotor, and the supernatant fluid was removed. The cDNA pellet was dried and was dissolved in TE buffer (pH 7.5) such that the concentration was about 20 ng µl.

Twenty five ng of the phosphorylated cDNA, 2 µl (1 µg) of λgt 10 arm, 1 µl of the L/K buffer solution and the sterilized water were added over an ice bath so that the total amount was 9 µl. It was mildly mixed and was centrifuged for several seconds using Eppendolf's rotor. After 1 µl (2.5 units) of T4 DNA ligase was mildly mixed, the mixture was incubated in a water bath maintained at 15° C. for 20 hours. The centrifugation was effected for several second using Eppendolf's rotor to collect the reaction solution in the bottom of the tube, and 10 µl of the whole amount of ligation reaction solution was packed in vitro to prepare cDNA libraries in a number of 500,000.

Example 2

Screening of SCC antigen cDNA.

Two spots (FIG. 1, underlined portions) were selected from the amino acid sequence of SCC antigen that has been partly determined, and mixed primers (primers 1,2 and primers 3,4; SEQ ID NOS:3–6, respectively) consisting of self-complementary 17 bases for all possible codon sequences was prepared by using a DNA synthesizer (381A, ABE Co.). Here, the primers 2,3 are anti-sense chains, and primers 1,4 are mixed primers that are in agreement with the sequences of the sense chains (Table 2). In the primers 1 and 2, however, the codon (AAC/U) for Asn was specified as AAC in order to reduce degeneracy. By using the primer 1 (100 pmol) and primer 3 (100 pmol) or the primer 2 (100 pmol) and primer 4 (100 pmol) as well as 2.5 units of DNA polymerase (AmpliTaq™, Takara Shuzo Co., Japan) and using cDNA (100 ng) as a template, the PCR was carried out 30 cycles (denaturation at 94° C. for 1 minute, annealing at 37° C. for 1.5 minutes, extension reaction at 72° C. for 3 minutes) at a final concentration of 50 mM potassium chloride, 10 mM Tris-HCl buffer solution (pH 8.3), 1.5 mM magnesium chloride, 0.01% (w/v) gelatin, and 200 µM dATP, dGTP, dCTP and dTTP. Furthermore, one-tenth amount of the DNA produced by the PCR was subjected to the PCR for 25 cycles (denaturation at 94° C. for one minute, annealing at 55° C. for 1.5 minutes, extension reaction at 72° C. for three minutes) using the same primers, and the whole amount of the PCR product was subjected to the electrophoresis employing a 5% polyacrylamide gel. As a result, nine DNA fragments (190 bp (base pairs)–580 bp) were obtained by a combination of the primers 1 and 3.

Gels containing these DNA fragments were recovered. The gels were crushed using a 2.5 ml injector and to which was added 1 ml of TE buffer (pH 7.5), and the mixture was incubated overnight at 37° C., filtered through a siliconized cotton, and was precipitated in ethanol. The precipitate was dissolved in the 10 µl of sterilized water, and 7 µl out of it was incubated at 37° C. for one hour together with 2 µl of 5×ligase buffer solution [330 mM Tris-HCl buffer solution (pH 7.6), 33 mM magnesium chloride, 50 mM DTT, 0.5 mM ATP] and 1 µl (one unit) of T4 polynucleotide kinase (Takara Shuzo Co., Japan) for the phosphorylation. By using a DNA Ligation Kit (Takara Shuzo Co., Japan), the above product was linked to M13 mp18 (1.4 µg) that was cut by HincII, and the base sequence was determined in compliance with Sanger et al method. As a result, the amino acid sequence encoded by a DNA fragment consisting of 194 bp was in agreement with the amino acid sequence of SCC antigen that had been partly determined. The DNA fragment of 194 bp was labelled with $^{32}$P (specific activity; 8.8×10$^8$ cpm/μg) in compliance with Feinberg and Vogelstein's method by using Multiprime DNA labelling systems (Amersham.) and was used as a probe in order to screen 2×10$^5$ cDNA libraries by the method described below.

Plaques on plates were transferred onto a nylon filter (Hybondr™ N, Amersham), pre-washed with 3×SSC (0.15M sodium chloride, 0.015M sodium citrate), 0.1% SDS at 65° C. for three hours, and was pre-hybridized in 50% formamide, 5×Denhardt solution (0.02% Ficoll, 0.02% bovine serum albumin, 0.02% polyvinyl pyrrolidone), 0.1% SDS, 5×SSEP [0.18M sodium chloride, 0.01M sodium phosphate (pH 8.0), 1 mM EDTA] and 100 μg/ml of thermally denatured salmon sperm DNA solution at 37° C. for 7 hours. The hybridization was carried out for 15 hours in the presence of the probe labeled with $^{32}$P under the same conditions as those of the pre-hybridization. Then, the filter was washed in 2×SSC, 0.1% SDS at room temperature for one hour and in 0.1×SSC, 0.1% SDS at 50° C. for 30 minutes, and was subjected to the autoradiography overnight at −80° C. As a result, there was obtained one positive clone (λSCC1, 1.6 kb).

A phage DNA was recovered from the positive clone and a restriction map was prepared. By using restriction enzymes (TaqI, EcoRI, HindIII, PstI, SphI), the positive clone DNA was cut and sub-cloned into M13 mp18, M13 mp19 vectors in order to determine base sequences. Since there was contained no translational initiation region, unique primers (primers 5, 7, 8) (FIG. 2 and 3) were prepared that were in agreement with the base sequence on the 5' terminal side of the clone (sense chain from 379 nucleotide (nt) to 399 nt from 5' terminus of λSCC1) and the base sequences of the upstream (from 52 nt to 33 nt on the upstream side of the restriction site) and the downstream (from 35 nt to 12 nt on the downstream side of the restriction site) of the EcoRI restriction site of the λgt 10 vector (SEQ ID NO:11), and were subjected to the PCR for 30 cycles (denatured at 94° C. for one minute, annealed at 50° C. for two minutes, elongated at 72° C. for three minutes) by using a primer 7 or 8 (100 pmol), a primer 5 (100 pmol) and 2.5 units of DNA polymerase (AmpliTaq™, Takara Shuzo Co., Japan) and using a DNA (100 ng) prepared from the cDNA library as a template at a final concentration of 50 mM potassium chloride, 10 mM Tris-HCl buffer solution (pH 8.3), 1.5 mM magnesium chloride, 0.01% (w/v) gelatin, 200 μM dATP, dGTP, dCTP and dTTP. The PCR product was subjected to the electrophoresis in a 3% NuSieve™ GTG agarose (FMC Bio Product Co.) to obtain fragments consisting of about 510 bp from the primers 5 and 7. In order to enhance the specificity of PCR, a unique primer (primer 6 in FIG. 2) was prepared that was in agreement with the upstream side (sense chain of from 287 nt to 307 nt from the 5' terminal of λSCC1) of the position where the primer 5 is hybridized, and was subjected to the PCR by using the primers 6 and 7, and a DNA fragment (10 ng) of 510 bp recovered from the NuSieve™ agarose using GENECLEAN™ II kit (BIO 101 Co.) as a template under the same conditions as those mentioned above, in order to obtain a fragment of about 420 bp.

After the restriction sites were digested with XbaI and SacI added to the primers, the base sequence (pcSCC 2) of cDNA amplified by being connected to the XbaI and SacI sites of M13 mp18 and M13 mp19 was determined and it was found that λSCC 1 and pcSCC 2 were overlapped for 307 bp. The E. coli strain carrying the expression plasmid PKK SCC1 in which a portion of from the sixty-second to the seventeen hundred-eleventh of SCC antigen cDNA (from 62 nt to 1711 nt of the base sequence of FIG. 4 and SEQ ID NO:1) are inserted in the E. coli expression vector PKK233-2, has been deposited in the Fermentation Research Institute Agency of Industrial Science and Technology, MITI, Japan, as Microorganism Deposit Accession No. 11871 (FERMP-11871).

FIG. 5 shows a restriction map of SCC cDNA clone and the direction and length of base sequence determination. As a result, the base sequence of SCC antigen cDNA (1693 bp, excluding poly(A) tail region) and the amino acid sequence (390 amino acids) estimated therefrom were determined (SEQ ID NO:1). The amino acid sequence was in agreement with the amino acid sequence of the fragment that had been partly determined. The fragment 13 (SEQ ID NO:13) only, however, was not in agreement (113 to 117 amino acids have a continuous 5 amino acid sequence that are in agreement with those of the fragment 13).

Further, the two hundred and fiftieth amino acid (SEQ ID NO:2) was different from the one determined by the amino acid analysis (Gln→Glu).

Sequences (Asn-X-Ser/Thr) to which aspartic-bonded sugar chain can be bonded were recognized at four sites in the determined base sequence. However, retrieval by using the data base of a computer in regard to homology indicated that the amino acid sequence was entirely homogeneous to the family of serine protease inhibitors (Serpins) from which it was confirmed that the SCC antigen has a probability of being used as a therapeutic drug to exhibit serine protease inhibitor activities.

Example 3

Identification of SCC antigen gene in a human genomic DNA by the Southern blotting.

Figure 6:
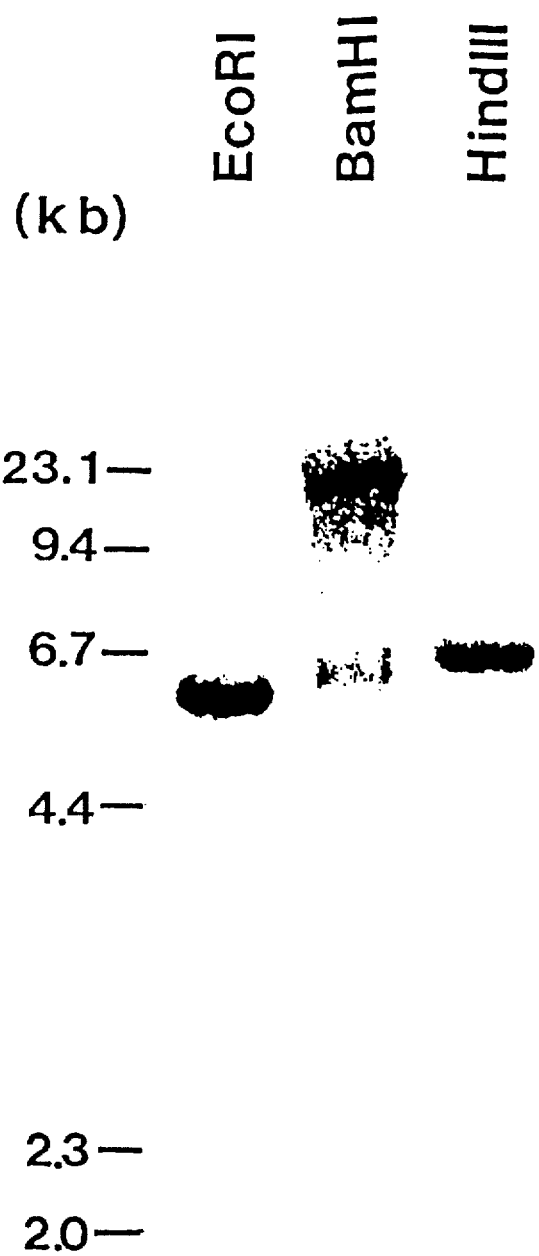
FIG. 6 shows bands of an autoradiography of when an SCC antigen gene in the human genomic DNA is identified by the Southern blotting.

The SCC antigen gene was analyzed by the Southern blotting using parts of the DNA sequence obtained according to the present invention. That is, a high molecular human genomic DNA was obtained from the peripheral blood leukocyte, 1 μg of the DNA was cut with a restriction enzyme, treated with phenol, precipitated in ethanol, dissolved in a TE buffer (pH 7.5), and was subjected to the electrophoresis employing a 0.8% agarose gel. After alkaliblotting onto a nylon filter (Hybond™ N+, Amersham) with a 0.4M sodium hydroxide, the filter was pre-hydridized at 37° C. for 4 hours in 50% formamide, 5×Denhart (0.1% Ficoll, 0.1% bovine serum albumin, 0.1% polyvinyl pyrrolidone), 5×SSPE (0.9M sodium chloride, 0.05M sodium phosphate, 5 mM EDTA pH 8.0), 0.5% SDS, 20 μg/ml salmon sperm DNA. The λSCC1 was sub-cloned to the EcoRI site of pUC 118, and an SphI fragment (1436 bp) was labelled and added (specific activity; 6.6×10$^8$ cpm/μg) by Feinberg and Vogelstein's method and was hybridized at 37° C. for 24 hours. The product was washed twice with 2×SSPE, 0.1% SDS (37° C.) for 20 minutes and was put to the autoradiography overnight at −80 ° C. One or two distinct bands were recognized. The product was washed again twice with 0.1×SSPE, 0.1% SDS (37° C.) for 30 minutes and was applied to the autoradiography. There developed no change in the pattern of one or two bands (FIG. 6) from which it was considered that the SCC antigen gene was in one copy only without any other related genes.

Amino acid sequences of SCC antigen that has been partly determined are shown in FIG. 1 (SEQ ID NOS:12–17). The underlined portions represent sequences that correspond to the primers 1, 2 (fragment 19) and primers 3, 4 (fragment 21-1), and X denotes amino acid which has not been confirmed yet, and parentheses represent amino acids that are estimated.

FIG. 2 shows oligodeoxynucleotide primers for PCR (SEQ ID NOS:3–10). The primers 1 and 4 are mixed primers in agreement with the sequences of the sense chain side estimated from the amino acid sequences underlined in FIG. 1 and the primers 2 and 3 are mixed primers in agreement with the sequences of the anti-sense chain side. The primers 5 and 6 are unique primers in agreement with the base sequence of the 5' side of λSCC1 and the primers 7 and 8 are unique primers in agreement with the base sequences of the upstream side and downstream side of EcoRI restriction site of the λgt 10 vector (SEQ ID NO:11). The XbaI site was added to the primers 5 and 6 on the 5' side and the SacI site was added to the primers 7 and 8 on the 5' terminal side.

FIG. 3 shows the EcoRI restriction site of the λgt 10 vector and the sites where primers 7 and 8 are hybridized.

FIG. 4 shows amino acid sequences (SEQ ID NO:2) that are estimated to be base sequences of SCC cDNA (SEQ ID NO:1). The pcSCC2 is from nucleotide No. 1 to No. 370 of the upper sequence, and λSCC1 is from 64 to 1711. Amino acid sequences are shown under the base sequences. Arrows indicate positions of the primers 6, 5, 3 and 1 in this order from the 5' terminal side. Portions indicated by boxes represent those portions (fragments 21-2=26, 10, 21-1, 19 in this order from the N terminal side) that are in agreement with the amino acid sequences of SCC antigen that has been partly determined. A dotted line represents a site which is in agreement with an sequence (Asn-X-Ser/Thr) to which aspartic-bonded sugar chains can be bonded. A double underline represents a poly(A) signal.

Advantages of the Invention

The present invention makes it possible to obtain the SCC antigen in large amounts by expressing a gene which codes for the squamous cell carcinoma associated antigen by using a known host such as E. coli, mammal cells or the like. The above antigen and the antibody obtained therefrom are used for the detection of SCC antigen by the immunological method.

Moreover, the gene which codes for the SCC antigen of the present invention can be effectively used as a probe for detecting SCC antigenic genes relying on the nucleic acid hybridization.

What is claimed is:

1. A method for recombinant production of human squamous cell carcinoma-associated antigen which comprises cultivating a host cell containing an expression vector comprising an isolated nucleic acid consisting of a nucleotide sequence coding for a polypeptide having an amino acid sequence of any one of SEQ ID NO:12, SEQ ID NO:13, SEQ ID NO:14, SEQ ID NO:15, SEQ ID NO:16 or SEQ ID NO:17, under conditions for sufficient for expression of said polypeptide.

2. An isolated nucleic acid consisting of SEQ ID NO:3.

3. An isolated nucleic acid consisting of SEQ ID NO:4.

4. An isolated nucleic acid consisting of SEQ ID NO:5.

5. An isolated nucleic acid consisting of SEQ ID NO:6.

6. An isolated nucleic acid consisting of a nucleotide sequence encoding an antigen consisting of the amino acid sequence of SEQ ID NO:2.

* * * * *

UNITED STATES PATENT AND TRADEMARK OFFICE
CERTIFICATE OF CORRECTION

PATENT NO. : 5,783,422
DATED : July 21, 1998
INVENTOR(S) : Yoshinori Suminami, et al.

It is certified that error appears in the above-identified patent and that said Letters Patent is hereby corrected as shown below:

Title page, [56] References Cited,
OTHER PUBLICATIONS: "Antien" should read -- Antigen --

Column 5,
Line 59: "Oilgotex" should read -- Oligotex --

Column 7,
Line 60: "layer" should read -- layers --

Column 10,
Line 43: "1µg" should read -- 10µg --

Column 21, Claim 1,
Line 33: "having" should read -- consisting of --

Signed and Sealed this

Eighteenth Day of September, 2001

Attest:

*Nicholas P. Godici*

NICHOLAS P. GODICI
*Attesting Officer*　　*Acting Director of the United States Patent and Trademark Office*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1711 base pairs
( B ) TYPE: nucleic acid
( C ) STRANDEDNESS: both
( D ) TOPOLOGY: linear ( i i ) MOLECULE TYPE: cDNA to mRNA ( i x ) FEATURE:
( A ) NAME/KEY: CDS
( B ) LOCATION: 62..1234

( x i ) SEQUENCE DESCRIPTION: SEQ ID NO:1:

```
CTCTCTGCCC ACCTCTGCTT CCTCTAGGAA CACAGGAGTT CCAGATCACA TCGAGTTCAC      60

CATGAATTCA CTCAGTGAAG CCAACACCAA GTTCATGTTC GACCTGTTCC AACAGTTCAG     120

AAAATCAAAA GAGAACAACA TCTTCTATTC CCCTATCAGC ATCACATCAG CATTAGGGAT     180

GGTCCTCTTA GGAGCCAAAG ACAACACTGC ACAACAGATT AAGAAGGTTC TTCACTTTGA     240

TCAAGTCACA GAGAACACCA CAGGAAAAGC TGCAACATAT CATGTTGATA GGTCAGGAAA     300

TGTTCATCAC CAGTTTCAAA AGCTTCTGAC TGAATTCAAC AAATCCACTG ATGCATATGA     360

GCTGAAGATC GCCAACAAGC TCTTCGGAGA AAAACGTAT CTATTTTAC AGGAATATTT       420

AGATGCCATC AAGAAATTTT ACCAGACCAG TGTGGAATCT GTTGATTTTG CAAATGCTCC     480

AGAAGAAAGT CGAAAGAAGA TTAACTCCTG GGTGGAAAGT CAAACGAATG AAAAAATTAA     540

AAACCTAATT CCTGAAGGTA ATATTGGCAG CAATACCACA TTGGTTCTTG TGAACGCAAT     600

CTATTTCAAA GGGCAGTGGG AGAAGAAATT TAATAAAGAA GATACTAAAG AGGAAAAATT     660

TTGGCCAAAC AAGAATACAT ACAAGTCCAT ACAGATGATG AGGCAATACA CATCTTTTCA     720

TTTTGCCTCG CTGGAGGATG TACAGGCCAA GGTCCTGGAA ATACCATACA AAGGCAAAGA     780

TCTAAGCATG ATTGTGTTGC TGCCAAATSA AATCGATGGT CTCCAGAAGC TTGAAGAGAA     840
```

-continued

```
ACTCACTGCT GAGAAATTGA TGGAATGGAC AAGTTTGCAG AATATGAGAG AGACACGTGT      900
CGATTTACAC TTACCTCGGT TCAAAGTGGA AGAGAGCTAT GACCTCAAGG ACACGTTGAG      960
AACCATGGGA ATGGTGGATA TCTTCAATGG GGATGCAGAC CTCTCAGGCA TGACCGGGAG     1020
CCGCGGTCTC GTGCTATCTG GAGTCCTACA CAAGGCCTTT GTGGAGGTTA CAGAGGAGGG     1080
AGCAGAAGCT GCAGCTGCCA CCGCTGTAGT AGGATTCGGA TCATCACCTG CTTCAACTAA     1140
TGAAGAGTTC CATTGTAATC ACCCTTTCCT ATTCTTCATA AGGCAAAATA AGACCAACAG     1200
CATCCTCTTC TATGGCAGAT TCTCATCCCC GTAGATGCAA TTAGTCTGTC ACTCCATTTG     1260
GAAAATGTTC ACCTGCAGAT GTTCTGGTAA ACTGATTGCT GGCAACAACA GATTCTCTTG     1320
GCTCATATTT CTTTCTTTC TCATCTTGAT GATGATCGTC ATCATCAAGA ATTTAATGAT      1380
TAAAATAGCA TGCCTTTCTC TCTTTCTCTT AATAAGCCCA CATATAAATG TACTTTTTCT     1440
TCCAGAAAAA TTCTCCTTGA GGAAAAATGT CCAAAATAAG ATGAATCACT TAATACCGTA     1500
TCTTCTAAAT TTGAAATATA ATTCTGTTTG TGACCTGTTT TAAATGAACC AAACCAAATC     1560
ATACTTTTTC TTTGAATTTA GCAACCTAGA AACACACATT TCTTTGAATT TAGGTGATAC     1620
CTAAATCCTT CTTATGTTTC TAAATTTTGT GATTCTATAA AACACATCAT CAATAAAATA     1680
GTGACATAAA ATCAAAAAAA AAAAAAAAA A                                     1711
```

( 2 ) INFORMATION FOR SEQ ID NO:2:

( i ) SEQUENCE CHARACTERISTICS:
        ( A ) LENGTH: 390 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Ser Leu Ser Glu Ala Asn Thr Lys Phe Met Phe Asp Leu Phe
  1               5                  10                  15
Gln Gln Phe Arg Lys Ser Lys Glu Asn Asn Ile Phe Tyr Ser Pro Ile
                 20                  25                  30
Ser Ile Thr Ser Ala Leu Gly Met Val Leu Leu Gly Ala Lys Asp Asn
                 35                  40                  45
Thr Ala Gln Gln Ile Lys Lys Val Leu His Phe Asp Gln Val Thr Glu
         50                  55                  60
Asn Thr Thr Gly Lys Ala Ala Thr Tyr His Val Asp Arg Ser Gly Asn
 65                  70                  75                  80
Val His His Gln Phe Gln Lys Leu Leu Thr Glu Phe Asn Lys Ser Thr
                     85                  90                  95
Asp Ala Tyr Glu Leu Lys Ile Ala Asn Lys Leu Phe Gly Glu Lys Thr
                100                 105                 110
Tyr Leu Phe Leu Gln Glu Tyr Leu Asp Ala Ile Lys Lys Phe Tyr Gln
            115                 120                 125
Thr Ser Val Glu Ser Val Asp Phe Ala Asn Ala Pro Glu Glu Ser Arg
        130                 135                 140
Lys Lys Ile Asn Ser Trp Val Glu Ser Gln Thr Asn Glu Lys Ile Lys
145                 150                 155                 160
Asn Leu Ile Pro Glu Gly Asn Ile Gly Ser Asn Thr Thr Leu Val Leu
                165                 170                 175
Val Asn Ala Ile Tyr Phe Lys Gly Gln Trp Glu Lys Lys Phe Asn Lys
            180                 185                 190
Glu Asp Thr Lys Glu Glu Lys Phe Trp Pro Asn Lys Asn Thr Tyr Lys
```

|  |  |  |  |  | 195 |  |  |  |  | 200 |  |  |  |  | 205 |  |  |  |
|---|---|---|---|---|---|---|---|---|---|---|---|---|---|---|---|---|---|---|
| Ser | Ile | Gln | Met | Met | Arg | Gln | Tyr | Thr | Ser | Phe | His | Phe | Ala | Ser | Leu |
| 210 | | | | | 215 | | | | | 220 | | | | | |
| Glu | Asp | Val | Gln | Ala | Lys | Val | Leu | Glu | Ile | Pro | Tyr | Lys | Gly | Lys | Asp |
| 225 | | | | | 230 | | | | | 235 | | | | | 240 |
| Leu | Ser | Met | Ile | Val | Leu | Leu | Pro | Asn | Glu | Ile | Asp | Gly | Leu | Gln | Lys |
| | | | | 245 | | | | | 250 | | | | | 255 | |
| Leu | Glu | Glu | Lys | Leu | Thr | Ala | Glu | Lys | Leu | Met | Glu | Trp | Thr | Ser | Leu |
| | | | 260 | | | | | 265 | | | | 270 | | | |
| Gln | Asn | Met | Arg | Glu | Thr | Arg | Val | Asp | Leu | His | Leu | Pro | Arg | Phe | Lys |
| | | 275 | | | | | 280 | | | | | 285 | | | |
| Val | Glu | Glu | Ser | Tyr | Asp | Leu | Lys | Asp | Thr | Leu | Arg | Thr | Met | Gly | Met |
| 290 | | | | | 295 | | | | | 300 | | | | | |
| Val | Asp | Ile | Phe | Asn | Gly | Asp | Ala | Asp | Leu | Ser | Gly | Met | Thr | Gly | Ser |
| 305 | | | | | 310 | | | | | 315 | | | | | 320 |
| Arg | Gly | Leu | Val | Leu | Ser | Gly | Val | Leu | His | Lys | Ala | Phe | Val | Glu | Val |
| | | | | 325 | | | | | 330 | | | | | 335 | |
| Thr | Glu | Glu | Gly | Ala | Glu | Ala | Ala | Ala | Thr | Ala | Val | Val | Gly | Phe | |
| | | | 340 | | | | | 345 | | | | 350 | | | |
| Gly | Ser | Ser | Pro | Ala | Ser | Thr | Asn | Glu | Glu | Phe | His | Cys | Asn | His | Pro |
| | | 355 | | | | | 360 | | | | | 365 | | | |
| Phe | Leu | Phe | Phe | Ile | Arg | Gln | Asn | Lys | Thr | Asn | Ser | Ile | Leu | Phe | Tyr |
| | 370 | | | | | 375 | | | | | 380 | | | | |
| Gly | Arg | Phe | Ser | Ser | Pro | | | | | | | | | | |
| 385 | | | | | 390 | | | | | | | | | | |

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

GCRTCNCCGT TRAADAT 17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:4:

ATHTTYAACG GNGAYGC 17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:5:

CCNAAYCARA THGAYGG 17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:6:

CCRTCDATHT GRTTNGG 17

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

TTTCTAGAAC AGATTCCACA CTGGTCTGG 29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:8:

TTTCTAGAGA TCTTCAGCTC ATATGCATC 29

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:9:

GGGAGCTCGC TGGGTAGTCC CCACCTTT 28

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:10:

GGGAGCTCCT TATGAGTATT TCTTCCAGGG TA 32

(2) INFORMATION FOR SEQ ID NO:11:

( i ) SEQUENCE CHARACTERISTICS:
  ( A ) LENGTH: 120 base pairs
  ( B ) TYPE: nucleic acid
  ( C ) STRANDEDNESS: both
  ( D ) TOPOLOGY: linear ( i i ) MOLECULE TYPE: DNA (genomic)

( x i ) SEQUENCE DESCRIPTION: SEQ ID NO:11:

```
CGAGCTGCTC TATAGACTGC TGGGTAGTCC CCACCTTTTG AGCAAGTTCA GCCTGGTTAA      60
GTCCAAGCTG AATTCTTTTG CTTTTACCC TGGAAGAAAT ACTCATAAGC CACCTCTGTT     120
```

( 2 ) INFORMATION FOR SEQ ID NO:12:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

```
Val Leu Glu Ile Pro Tyr Lys
 1               5
```

( 2 ) INFORMATION FOR SEQ ID NO:13:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:13:

```
Tyr Leu Phe Leu Xaa Tyr Glu Arg Phe Ser Val Pro
 1               5                  10
```

( 2 ) INFORMATION FOR SEQ ID NO:14:

( i ) SEQUENCE CHARACTERISTICS:
    ( A ) LENGTH: 23 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:14:

```
Gly Met Val Xaa Ile Phe Asn Gly Asp Ala Asp Leu Ser Gly Met Thr
 1               5                  10                  15
Gly Ser Arg Gly Leu Val Leu
                20
```

( 2 ) INFORMATION FOR SEQ ID NO:15:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:15:

```
Xaa Leu Ser Met Ile Val Leu Leu Pro Asn Gln Ile Asp Gly Leu Gln
 1               5                  10                  15
Lys
```

(2) INFORMATION FOR SEQ ID NO:16:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:16:

```
Xaa Met Phe Xaa Leu Phe Gln Gln Phe Arg Lys
1               5                   10
```

(2) INFORMATION FOR SEQ ID NO:17:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:17:

```
Phe Met Phe Asp Leu Phe
1               5
```